(12) United States Patent
Lee et al.

(10) Patent No.: US 8,354,386 B2
(45) Date of Patent: Jan. 15, 2013

(54) PHARMACEUTICAL COMPOSITION FOR TREATING MALIGNANT TUMORS CONTAINING HUMAN P31 GENES

(75) Inventors: Kee-Ho Lee, Seoul (KR); Sang-Hoon Kim, Seoul (KR); Hyun-Jung Baek, Seoul (KR); Kyoung-Mi Juhn, Seoul (KR); Jae-Min Jeong, Seoul (KR); Yeun-Jin Ju, Seoul (KR); Bu-Yeo Kim, Seoul (KR); Eun-Ju Lee, Seoul (KR); Yong-Ho Ham, Seoul (KR); Hee-Chung Kwon, Seoul (KR); Mi-Yong Yun, Namyangju (KR); Gil-Hong Park, Seoul (KR)

(73) Assignee: Korea Institute of Radiological & Medical Sciences (KR)

( * ) Notice: Subject to any disclaimer, the term of this patent is extended or adjusted under 35 U.S.C. 154(b) by 514 days.

(21) Appl. No.: 12/095,672

(22) PCT Filed: Dec. 20, 2005

(86) PCT No.: PCT/KR2005/004385
§ 371 (c)(1),
(2), (4) Date: Aug. 2, 2010

(87) PCT Pub. No.: WO2007/064057
PCT Pub. Date: Jun. 7, 2007

(65) Prior Publication Data
US 2010/0292166 A1    Nov. 18, 2010

(30) Foreign Application Priority Data
Nov. 30, 2005    (KR) .................. 10-2005-0115899

(51) Int. Cl.
*A61K 48/00*    (2006.01)
*C12N 15/11*    (2006.01)
(52) U.S. Cl. .................................. 514/44 R; 435/320.1
(58) Field of Classification Search .................. 514/44 R
See application file for complete search history.

(56) References Cited

FOREIGN PATENT DOCUMENTS
KR    10-2003-0013951    2/2003
WO    99/43843    9/1999

OTHER PUBLICATIONS

Habu et al.; Identification of a MAD2-binding protein, CMT2, and its role in mitosis; EMBO; vol. 21 No. 23: 6419-6428 (2002).*
Patil et al.; DNA-based therapeutics and DNA delivery systems: a comprehensive review; The AAPS Journal, 7(1): Article 9, E61-E77, 2005.*
European Search Report for Application No. 05822033.6-2405/1951317, PCT/KR2005/004385 dated Jan. 13, 2009.
Darren J. Baker et al., The Mitotic checkpoint in cancer and aging: what have mice taught us?, Current Opinion in Cell Biology, Current Science, London, GB, Oct. 13, 2005, vol. 17, No. 6, pp. 583-589.
Toshiyuki Habu et al., Indentification of a MAD2-binding protein, CMT2, and its role in mitosis, European Molecular Biology Organization, The Embo Journal, 2002, vol. 21, No. 23, Oct. 18, 2002, pp. 6419-6428.
Arun Sreekumar et al., Profiling of Cancer Cells Using Protein Microarrays: Discovery of Novel Radiation-regulated Proteins, Cancer Research, vol. 61, Oct. 15, 2001, pp. 7585-7593.
pQCXIN Retroviral Vector Information, Clontech Laboratories, Inc., Protocol No. PT3667-5, Version No. PR23865, Mar. 25, 2002, pp. 1-3.
BD Retro-X Q Vectors, New self-inactivating vectors engineered to produce higher titers, BD Biosciences Clontech, Clontechniques, Jul. 2002.
International Search Report-PCT/KR2005/004385 dated Aug. 21, 2006.
Written Opinion-PCT/KR2005/004385 dated Aug. 21, 2006.

* cited by examiner

*Primary Examiner* — Michele K Joike
*Assistant Examiner* — Antonio Galisteo Gonzalez
(74) *Attorney, Agent, or Firm* — Cantor Colburn LLP

(57) ABSTRACT

A pharmaceutical composition for the treatment of malignant tumors comprising a human $p31^{comet}$ gene encoding protein represented by SEQ ID NO: 3 or 4 as an effective component is provided. The pharmaceutical composition can suppress cancer cell growth, induce apoptosis and kill cells by overexpressing $p31^{comet}$ in the solid malignant tumor cells. Therefore, the pharmaceutical composition can be effectively used for gene therapy.

8 Claims, 5 Drawing Sheets

PHARMACEUTICAL COMPOSITION FOR TREATING MALIGNANT TUMORS CONTAINING HUMAN P31 GENES

TECHNICAL FIELD

The present invention relates to a pharmaceutical composition for the treatment of malignant tumors by expressing human p31$^{comet}$ in various malignant tumors, and more particularly, to a pharmaceutical composition containing a human p31$^{comet}$ gene encoding protein represented by SEQ ID NO: 3 or 4 as an effective component. Cancers can be cured by infecting malignant tumor cells with an adenovirus or retrovirus including the p31$^{comet}$ gene and expressing the p31$^{comet}$ protein to kill the cancer cells and suppress the growth of the cancer cells.

BACKGROUND ART

In general, cancer refers to the uncontrolled proliferating of cells. Lumps of such cells are classified into malignant tumors that lead to the death of an individual, and benign tumors that do not cause death. It can sometimes be difficult to accurately classify tumors. Most cancers are induced by cancer-triggered genes or mutations in cancer-inhibiting genes. The proliferation of cells regulates cell differentiation, a signal transduction system controlling the cell cycle and signal transduction between cells. When the regulation is abnormally performed, the cells cannot be differentiated and ceaseless proliferation is induced. This process is called carcinogenesis. If a method of correcting the abnormal regulation of the cancer-triggered protein is found, such a method would possibly be the most effective anti-cancer medicine without nonspecific effects.

Currently, cancer patients are treated through surgery, chemotherapy and radiation therapy. Substantially, complex cancer treatments combining such therapies and laser surgery are used. Chemotherapy is used prior to other treatments to reduce pain during treatment or to prevent the spread of cancer. Many anti-cancer agents have been discovered through much research, and most of them focus on selectively killing vigorously dividing cells. However, such agents cannot be used for long term treatment due to the side effects of killing normal cells such as immune cells or hair follicle cells.

Most anti-cancer agents destroy cancer cells by suppressing the synthesis of nucleic acids or interrupting cell metabolisms directly bound to the nucleic acids. Generally, anti-cancer agents cannot selectively attack malignant tumors. Anti-cancer agents attack and damage vigorously dividing normal cells such as hair, haemopietic cells in bone marrow, mucosal gastric cells and intestinal mucosa cells to cause side effects such as depilation, anemia, leukopenia, thrombocytopenia, gastric and intestinal mucosal damage. Besides causing side effects, conventional anti-cancer agents are not effective against tumors that spread to other tissues of the body.

Anti-cancer agents are classified into cytotoxic anti-cancer agents and hormonal anti-cancer agents. Examples of cytotoxic anti-cancer agents include Altretamine and Busulfan, and examples of hormonal anti-cancer agents include Tamoxipan and Toremifene. Cytotoxic anti-cancer agents transform into a material having a positive charge and covalently bind to a substance having plentiful electrons and ions such as nucleic acids, proteins and amino acids, thereby suppressing the synthesis of DNA and RNA. Hormonal anti-cancer agents bind to receptors of estrogen, thereby suppressing proliferation of estrogen dependent breast cancer cells.

In gene therapy, to treat genetic diseases and cancers caused by gene mutations, genes are directly inserted into cells having genes affected by a disease so that the function of the cells is normalized by expressing the inserted genes. The gene therapy can be widely used to prevent various diseases or to reinforce treatment by inserting a specific gene into a body cell and granting a new function to the body cell.

The most important factor in the treatment of diseases using gene therapy is that the inserted gene be successfully delivered to the nucleus of the target cell and that the gene be expressed strongly. The gene enters the target cell through endocytosis and is transported into the nucleus to be expressed. The gene can be inserted using a carrier such as a liposome since most DNAs are destroyed when entering the cell. However, most of the liposomes are also destroyed when entering the nucleus, thereby decreasing the transporting efficiency.

A virus capable of infecting a human can be treated using gene therapy because the virus effectively inserts exogeneous genes into the human body. Specifically, the gene can effectively be transported and expressed by inserting the gene for the gene therapy into the DNA of the virus using gene recombination and infecting human body with the recombinant virus, which can be mass produced in vitro. An adenovirus can be effectively used for the gene therapy by using a special mechanism of transporting the gene into the nucleus of the target cell with a high efficiency. In addition, retroviruses are being used in more than 50% of internationally permissible clinical trials (Wiley Online Library—The Journal of Gene Medicine). Retroviruses are effective for gene therapy when inserted into cell chromosomal DNA to allow long term expression of the desired protein.

One of the features of tumor cells is chromosomal abnormality such as aneuploid or tetraploid due to structural instability of chromosomes, or multinucleation. When spindle fiber check points lose the ability to regulate cell division, DNA synthesis is known to be carried out through endoreduplication (Jallepalli P V and Lengauer C. (2001). Nat. Rev. Cancer, 1, 109-117). Mad2 is an important protein delaying cell division until all spindle fibers are attached to the centromere (Hardwick K G, Johnston R C, Smith D L, Murray A W. J. Cell Biol. 2000 Mar. 6; 148(5):871-82). A recent article reported that while a partial loss of Mad2 promotes multinucleation, resulting in cancer (Dobles M, Liberal V, Scott M L, Benezra R and Sorger P K. 2000. Cell, 101, 635-645), and a complete loss of Mad2 using siRNA generates a signal inducing death of cancer cell line (Michel L, Diaz-Rodriguez E, Narayan G, Hernando E, Murty V V, Benezra R. Proc Natl Acad Sci USA 2004; 1001:4459-64; Kops G J, Foltz D R, Cleveland D W., Proc Natl Acad Sci USA. 2004 Jun. 8; 101:8699-704). P31$^{comet}$ is a protein that regulates Mad2 by interacting with Mad2 bound to APC/C$^{Cdc20}$ when a mitosis check point is activated during the metaphase of cell division (Habu T, Kim S H, Weinstein J and Matsumoto T. 2002. EMBO J., 21; 6419-6428). P31$^{comet}$ also promotes the activity of APC/C suppressed by Mad2. These features show that p31$^{comet}$ functions against Mad2 (Xia G, Luo X, Habu T, Rizo J, Matsumoto T, Yu H., EMBO J. 2004 Aug. 4; 23(15):3133-43).

Therefore, the inventors of the present invention conducted research based on the idea that overexpression of p31$^{comet}$ in cancer cells can completely inhibit Mad2, thereby killing the cancer cell. The p31$^{comet}$ gene was introduced into an adenovirus vector and a retrovirus vector to effectively express p31$^{comet}$ in a cancer cell and viruses including p31$^{comet}$ were produced. The produced viruses were injected into various cancer cells and the expression of p31$^{comet}$ was identified. A fluorescence protein is designed to be expressed together with p31$^{comet}$ to distinguish expressed cancer cells from non-expressed cancer cells. In the cells infected with the retrovirus or adenovirus including p31$^{comet}$, it was found that the fluorescent cells are dead or the growth of the fluorescent cells stops after a certain period of time.

DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Technical Problem

The present invention provides a pharmaceutical composition for the treatment of malignant tumors including a human p31$^{comet}$ gene encoding protein represented by SEQ ID NO: 3 or 4 as an effective component.

The present invention also provides a recombinant virus vector pAdeno-CMV/p31$^{comet}$-IRES/GFP or Retro-IRES/p31$^{comet}$ that expresses p31$^{comet}$, and a microorganism transformed with the recombinant virus vector.

The present invention also provides a method of preparing a recombinant p31 comet protein by cultivating mammalian cells transfected with the recombinant virus vector.

The present invention also provides a pharmaceutical composition for the treatment of malignant tumors including the recombinant virus vector as an effective component.

The present invention also provides a pharmaceutical composition for the treatment of malignant tumors including p31$^{comet}$ RNA transcribed from the p31$^{comet}$ gene as an effective component.

The present invention also provides a pharmaceutical composition for the treatment of malignant tumors including a protein represented by SEQ ID NO: 3 or 4 as an effective component.

The present invention also provides a recombinant virus which does not include a transducted proliferous variant adenovirus or retrovirus.

The present invention also provides a microarray for the diagnosis of malignant tumors adhered to a support including the entire or part of a probe of a p31$^{comet}$ gene represented by SEQ ID NO: 1 or 2, or an antibody to a p31$^{comet}$ protein represented by SEQ ID NO: 3 or 4, and a diagnostic kit for malignant tumors including the microarray.

Technical Solution

According to an aspect of the present invention, there is provided a pharmaceutical composition for the treatment of malignant tumors including a human p31$^{comet}$ gene encoding protein represented by SEQ ID NO: 3 or 4 as an effective component. The human p31$^{comet}$ gene may be represented by SEQ ID NO: 1 or 2. The malignant tumor may be a solid malignant tumor of uterine cervix cancer, ovarian cancer, liver cancer, breast cancer, lung cancer, bone cancer, kidney cancer, pancreatic cancer, gastric cancer, or colorectal cancer.

Figure 6:
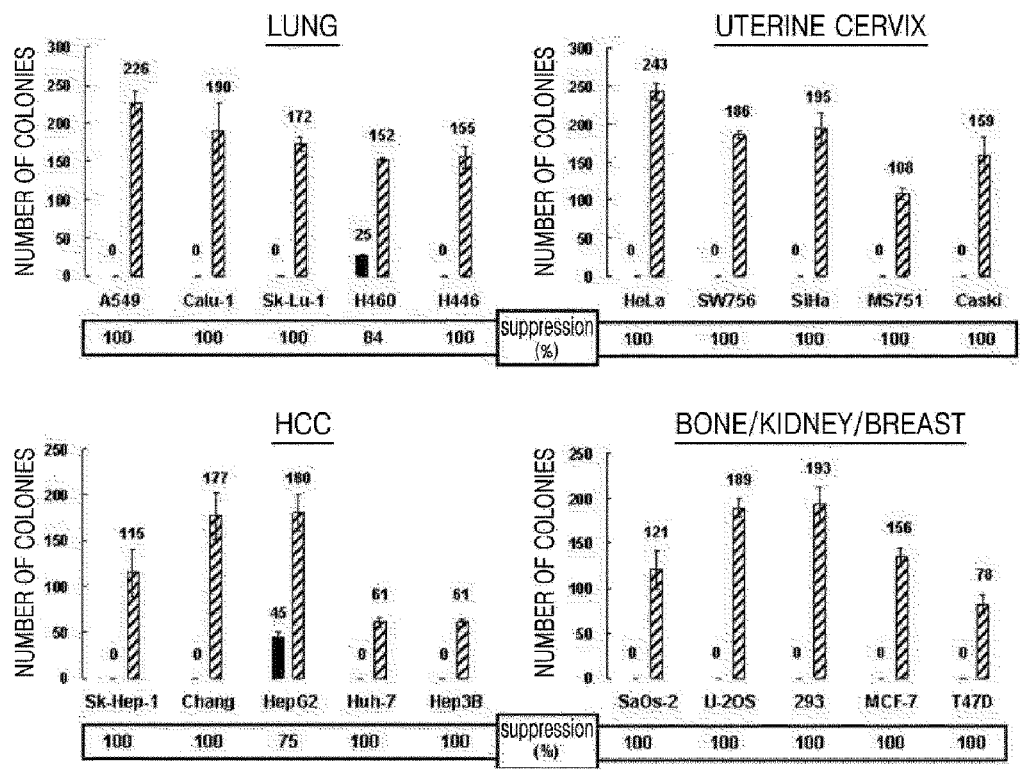
FIG. 6 shows the measured growth of various solid cancer cell lines derived from lung cancer, uterine cervix cancer, liver cancer, bone cancer, kidney cancer and breast cancer when p31$^{comet}$ was overexpressed.

The pharmaceutical composition suppresses cancer cell growth, induces apoptosis and kills the cell by overexpressing p31$^{comet}$ in the solid malignant tumor cells. p31$^{comet}$ can be classified into two types, one having 274 amino acids and a molecular weight of 34 kDa and the other having 306 amino acids and a molecular weight of 37 kDa. The expressed amount of p31$^{comet}$ increases in the mitotic phase of a cell cycle and decreases in the presynthesis phase of the cell cycle (Habu T, Kim S H, Weinstein J and Matsumoto T. 2002. EMBO J. 21; 6419-6428). p31$^{comet}$ regulates Mad2, which delays cell division through a cell division regulating system in response to an abnormal condition of cells. However, the inventors of the present invention discovered that p31$^{comet}$ suppresses cancer cell growth, induces apoptosis and kills the cell in addition to its function of regulating cell division. When overexpressing p31$^{comet}$ in 20 types of cancer cells from tissues of the liver, uterine cervix, lung, bone, kidney, breast, etc., the death of the cells or the blocking of the cell growth was identified (refer to FIG. 6).

The gene is referred to as p31$^{comet}$, and has also been referred to as CMT2. p31$^{comet}$ can have a nucleotide sequence length of 1,550 bp and is represented by SEQ ID NO: 1. In the nucleotide sequence of SEQ ID NO: 1, an open reading frame corresponding to the 209$^{th}$ to 1,129$^{th}$ nucleotides in which the 1,127$^{th}$ to 1,129$^{th}$ nucleotides are the termination codon is a region encoding a protein including 306 amino acids represented by SEQ ID NO: 3 (p31$^{comet}$-1). The p31$^{comet}$ gene can have a nucleotide sequence length of 1,283 bp and be represented by SEQ ID NO: 2. In the nucleotide sequence of SEQ ID NO: 2, an open reading frame corresponding to the 37$^{th}$ to 861$^{st}$ nucleotides in which the 859$^{th}$ to 861$^{st}$ nucleotides are the termination codon is a region encoding a protein including 274 amino acids represented by SEQ ID NO: 4 (p31$^{comet}$-2). However, various changes in encoding regions of p31$^{comet}$-1 and -2 genes may be made without changing the amino acid sequence of an oncogenic protein expressed by the encoding region considering the degeneracy of the codon or the preferred codon in an organism in which the gene is expressed. Additionally, various changes or modifications in non-coding regions may be made without influencing the gene expression. Polynucleotides having substantially the same sequences as p31$^{comet}$-1 and -2 genes represented by SEQ ID NOS: 1 and 2 and fragments of the p31$^{comet}$-1 and -2 genes can also be used. Herein, polynucleotides are substantially the same if the polynucleotides have at least 80% homology, preferably at least 90% homology, and most preferably at least 95% homology. The p31$^{comet}$-1 protein expressed by the p31$^{comet}$-1 gene includes 306 amino acids, has sequences of SEQ ID NO: 3 and has a molecular weight of 34 kDa, and p31$^{comet}$-2 protein expressed by p31$^{comet}$-2 gene includes 247 amino acids, has sequences of SEQ ID NO: 4 and has a molecular weight of 37 kDa. However, a substitution, addition or deletion of amino acids in the amino acid sequence of p31$^{comet}$-1 and -2 proteins may be made without influencing the function of the protein. A partial protein can also be used according to a desired purpose and altered amino acid sequences can also be used. Accordingly, polypeptides having substantially the same sequences as p31$^{comet}$-1 and -2 proteins and fragments of such polypeptides can also be used. Herein, polypeptides are substantially the same if the polypeptides have at least 80% homology, preferably at least 90% homology, and most preferably, at least 95% homology. p31$^{comet}$1 and -2 genes and proteins can be separated from human cancer tissues or synthesized using known DNA or peptide synthesizing methods. In addition, the prepared gene may be inserted into vectors for microorganism expression known in the field to prepare the expression vectors, and introduced into proper host cells such as E. coli or yeast cells. Mass replication of DNA or mass production of protein can be carried out using such transformed host cells. E. coli DH5α was transfected with a vector containing p31$^{comet}$-1 and -2 genes in Examples of the present invention. In the preparation of a vector, expression regulating sequences such as promoters and terminators, self-replication sequences and secretion signal sequences may be properly selected and combined according to the type of host cells in which p31$^{comet}$-1 and -2 genes are expressed and p31$^{comet}$-1 and -2 proteins are produced.

The pharmaceutical composition of an embodiment of the present invention may include a nucleic acid encoding p31$^{comet}$ protein and a pharmaceutically acceptable carrier or vehicle. The pharmaceutical composition is especially suitable for preparing a biological material for gene therapy.

Any vector, viral or non-viral, according to an embodiment of the invention is preferably introduced in vivo in a pharmaceutically acceptable vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The pharmaceutical compositions of embodiments of the invention may be formulated for the purpose of topical, oral, parenteral, intranasal, intravenous, intramuscular, subcutaneous, intraocular, and similar administrations.

Preferably, the pharmaceutical compositions contain pharmaceutically acceptable vehicles for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on appropriate addition of sterilized water or physiological saline, enable injectable solutions to be formed.

The compositions may be in particular isotonic, sterile, saline solutions (monosodium or disodium phosphate, sodium, potassium, calcium or magnesium chloride and the like or mixtures of such salts), or dry, particularly, freeze-dried, compositions which, upon appropriate addition of sterilized water or physiological saline, allow the constitution of injectable solutions.

The preferred sterile injectable preparation can be a solution or suspension in a nontoxic parenterally acceptable solvent or diluent. Examples of pharmaceutically acceptable carriers or vehicles are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil, such as a synthetic mono- or di-glyceride, can be employed. Fatty acids such as oleic acid also be used in the preparation of injectables.

The dose of nucleic acid of an embodiment of the invention used for administration, either alone or incorporated in a vector, can be adjusted according to different parameters, and, in particular, according to the mode of administration used, the pathology in question, the gene to be expressed or the desired treatment period. Generally speaking, the recombinant viruses according to embodiments of the invention are formulated and administered in the form of doses of between $10^4$ and $10^{14}$ pfu, and preferably $10^6$ to $10^{10}$ pfu. The term pfu (plaque forming unit) corresponds to the infectious power of a solution of a virus, and is determined by the infection of a suitable cell culture and measurement, generally after 48 hours, of the number of infected cell plaques. Techniques of determining the pfu titer of a viral solution are well documented in the literature.

The composition according to an embodiment of the invention may be introduced parenterally or transmucosally, e.g., orally, nasally, rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In yet another embodiment, a composition comprising a human p31$^{comet}$ polypeptide, or a nucleic acid encoding the polypeptide can be delivered in a controlled release system. For example, the nucleic acid or polypeptide may be administered using intravenous infusion, an implantable osmotic pump, a transdermal patch, liposomes, or another mode of administration.

Thus, the compositions according to embodiments of the invention can be delivered by an intravenous, intraarterial, intraperitoneal, intramuscular, or subcutaneous route of administration. Alternatively, the compositions can be properly formulated to be administered nasally or orally. A constant supply of the biological material can be ensured by providing a therapeutically effective dose (i.e., a dose effective to induce metabolic changes in a subject) at necessary intervals, e.g., daily, every 12 hours, etc. These parameters will depend on the severity of the disease being treated, other actions, such as diet modification, that are implemented, the weight, age, and sex of the subject, and other criteria, which can be readily determined according to standard medical practice by those of skill in the art.

An organism in which a biological material according to an embodiment of the invention is administered is preferably a human, but can be any animal. Thus, as can be readily appreciated by one of ordinary skill in the art, the methods and pharmaceutical compositions of embodiments of the present invention are particularly suited for administration to any animal, particularly, mammals, and including, but by no means limited to, domestic animals, such as feline or canine subjects; farm animals, such as, but not limited to, bovine, equine, caprine, ovine, and porcine subjects; wild animals (whether in the wild or in a zoological garden); research animals, such as mice, rats, rabbits, goats, sheep, pigs, dogs, cats, etc.; avian species, such as chickens, turkeys, songbirds; etc. That is, a biological material according to an embodiment of the invention is suitable for veterinary medical use.

In the pharmaceutical composition of an embodiment of the present invention, the $p31^{comet}$ gene can be delivered by a vector complexed with a virus such as a retrovirus, an adenovirus, an adeno-associated virus (AAV), a herpes simplex virus or the like. Preferably, the vector can be a recombinant adenovirus vector pAdeno-CMV/$p31^{comet}$-IRES/GFP or a recombinant retrovirus vector Retro-IRES/$p31^{comet}$.

Viral vectors commonly used for in vivo and ex vivo targeting and therapy procedures include DNA-based vectors and retroviral vectors. Methods or constructing and using viral vectors are known in the art [see, e.g., Miller and Rosman, BioTechniques 7:980-990 (1992)]. Preferably, the viral vectors are replication defective, that is, they are unable to replicate autonomously in the target cell. In general, the genome of a replication defective viral vector lacks at least one region which is necessary for the replication of the virus in the infected cell. Such a region can either be eliminated (in whole or in part), or be rendered non-functional using any technique known in the art. These techniques include the total removal, substitution (by other sequences, in particular by the inserted nucleic acid), partial deletion or addition of one or more bases in an essential (for replication) region. Such techniques may be performed in vitro (on the isolated DNA) or in situ, using the techniques of genetic manipulation or by treatment with mutagenic agents. Preferably, the genome of the replication defective virus retains the sequences which are necessary for encapsulating the viral particles.

DNA viral vectors include attenuated or defective DNA viruses, such as, but not limited to, herpes simplex virus (HSV), papillomavirus, Epstein Barr virus (EBV), adenovirus, adeno-associated virus (AAV), vaccinia virus, and the like. Defective viruses, which completely or almost completely lack viral genes, are preferred. A defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci. 2:320-330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as a vector described by Stratford-Perricaudet et al. [J. Clin. Invest. 90:626-630 (1992); see also La Salle et al., Science 259:988-990 (1993)]; and a defective adeno-associated virus vector [Samulski et al., J. Virol. 61:3096-3101 (1987); Samulski et al., J. Virol. 63:3822-3828 (1989); Lebkowski et al., Mol. Cell. Biol. 8:3988-3996 (1988)].

In an embodiment of the present invention, the vector is an adenovirus vector. Adenoviruses are eukaryotic DNA viruses that can be modified to efficiently deliver a nucleic acid of an embodiment of the present invention to a variety of types of cells. Various serotypes of adenoviruses exist. Of these serotypes, it is preferable to use, type 2 or type 5 human adenoviruses (Ad 2 or Ad 5) or adenoviruses of animal origin (see WO94/26914). Adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, and more preferably a CAV2 adenovirus (e.g. Manhattan or A26/61 strain (ATCC VR-800).

Preferably, the replication defective adenoviral vectors according to embodiments of the present invention include the ITRs, an encapsidation sequence and the nucleic acid of interest. It is further preferable that at least the E1 region of the adenoviral vector is non-functional. A deletion in the E1 region preferably extends from nucleotides 455 to 3329 in the sequence of the Ad5 adenovirus (PvuII-BgIII fragment) or nucleotides 382 to 3446 (Hinfll-Sau3A fragment). Other regions may also be modified; in particular the E3 region (WO95/02697), the E2 region (WO94/28938), the E4 region (WO94/28152, WO94/12649 and WO95/02697), or regions in any of the late genes L1-L5.

In an embodiment of the present invention, the adenoviral vector has a deletion in the E1 region (Ad 1.0). Examples of E1-deleted adenoviruses are disclosed in EP No. 185,573, the contents of which are incorporated herein by reference. In another embodiment of the present invention, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In another embodiment of the present invention, the adenoviral vector has a deletion in the E1 region into which the E4 region and the nucleic acid sequence are inserted (see FR94 13355, the contents of which are incorporated herein by reference).

The replication defective recombinant adenoviruses according to embodiments of the invention can be prepared using any technique known in the art (Levrero et al., Gene 101 (1991) 195, EP 185 573; Graham, EMBO J. 3 (1984) 2917). In particular, the replication defective recombinant adenoviruses can be prepared through homologous recombination between an adenovirus and a plasmid which carries, inter alia, the DNA sequence of interest. The homologous recombination is effected after cotransfection of the adenovirus and plasmid into an appropriate cell line. The cell line which is employed should preferably (i) be transformable by the said elements, and (ii) contain sequences which complement part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59), which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

In another embodiment of the present invention, the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; Dougherty et al., International Patent Publication No. WO 95/07358, published Mar. 16, 1995; and Kuo et al., 1993, Blood 82:845. The retroviruses are integrating viruses which infect dividing cells. The retrovirus genome includes two LTRs, an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retroviruses, such as HIV, murine Moloney leukaemia virus (MoMuLV), murine Moloney sarcoma virus (MSV), Harvey sarcoma virus (HaSV), spleen necrosis virus (SNV), Rous sarcoma virus (RSV) and Friend virus. Defective retroviral vectors are disclosed in WO95/02697.

In general, in order to construct recombinant retroviruses containing a nucleic acid sequence, a plasmid which contains the LTRs, the encapsulation sequence and the coding sequence is constructed. This plasmid is used to transfect a packaging cell line, which is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP$^+$envAm$^{-12}$ cell line (WO89/07150). In addition, the recombinant retroviral vectors can contain modifications within the LTRs for suppressing transcriptional activity as well as extensive encapsulation sequences which may include a part of the gag gene (Bender et al., J. Virol. 61 (1987) 1639). Recombinant retroviral vectors are purified using standard techniques known in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional viruses.

Targeted gene delivery is described in International Patent Publication WO 95/28494, published October 1995.

A promoter used in a vector including p31$^{comet}$ gene in the pharmaceutical composition according to an embodiment of the present invention can be a promoter such as insulin promoter, whey acidic protein promoter, tyrosinase promoter, glial fibrillary acidic protein promoter, albumin promoter, CEA promoter, T-cell receptor promoter, a-Fetoprotein (AFP) promoter, circulatory luekoprotease inhibitor (CLPI) promoter, Her 2/neu promoter, Myc-Max responsive element promoter, MUC-1 promoter, osteocalcin promoter, MCK promoter, MBP promoter, GFAP promoter, NSE promoter, prostate-specific antigen (PSA) promoter, prostate-specific membrane antigen (PSMA) promoter, probasin promoter, human glandular kallikrein (hK2) promoter, myelin basic protein (MBP) promoter, myelin proteolipid protein promoter, neural specific enolase promoter, neuronal specific synapsin 1 promoter, Ncx/Hox11L.1 promoter, surfactant protein B promoter, thyroglobulin promoter, ovarian-specific promoter, telomerase promoter, Erb B2 promoter, DF3/MUC1 promoter, L-plastin promoter, SLP1 promoter, alpha lactalbumin promoter, somatostatin promoter, Cox2 promoter, ornithine decarboxylase promoter, gastrin-releasing peptide promoter, metallothionein promoter, calponin promoter, H19 promoter, Tcf promoter, calretinin promoter, Cdc25C promoter, cyclin A promoter, endoglin promoter, IGF-1-R promoter, E2F-1 promoter, KDR/Flk-1 promoter, Flt-1 promoter, E-selectin promoter, vWF promoter, preproendothelin-1 promoter, VCAM-1 promoter, VEGF promoter, erythropoetin promoter, phosphoglycerate kinase 1 promoter, GRP78 promoter, hexokinase II promoter, Erg-1 and CArG elements promoter, Waf-1 promoter, RecA promoter, c-IAP2 promoter, HSP70B promoter, Gadd 153 promoter, MDR-1 promoter, tetracycline inducible promoter, rapamycin inducible promoter or tamoxifen-inducible estrogen response elements promoter.

According to another aspect of the present invention, there is provided a recombinant adenovirus vector pAdeno-CMV/p31$^{comet}$-IRES/GFP expressing the p31$^{comet}$ gene. The adenovirus expression vectors produce the p31$^{comet}$ protein using an expression cassette including a promoter site of Cytomegalovirus, a multiple cloning site, a late polyadenylation signal site of Simian virus 40 (SV40) and a site encoding Green fluorescence protein (GFP). Integration of the vector can be identified because the Green fluorescence protein is found when a cancer cell has been infected with the adenovirus expression vector. For this purpose, pAdenoVator-CMV5-IRES-GFP vector including the expression cassette containing a promoter site of Cytomegalovirus, a multiple cloning site, a late polyadenylation signal site of Simian virus 40 and a Green fluorescence protein (GFP) was used. RT-PCR was performed using RNA isolated from normal tissues as a template to obtain the normal human p31$^{comet}$ gene. The recombinant adenovirus expression vector pAdeno-CMV/p31$^{comet}$-IRES/GFP capable of expressing the p31$^{comet}$ protein was obtained using the obtained cDNA of p31$^{comet}$.

According to another aspect of the present invention, there is provided a recombinant retrovirus vector Retro-IRES/p31$^{comet}$ expressing the p31$^{comet}$ gene. Particularly, the recombinant retrovirus vector Retro-IRES/p31$^{comet}$ produces the p31 comet protein using an expression cassette including a 5' long terminal repeat (LTR) promoter site, a multiple cloning site, an internal ribosomal entry site (IRES), a gene encoding a Green fluorescence protein (GFP) or a selection protein (puromycin, hereinafter referred to as 'puro') and a late polyadenylation signal site in 3' LTR. Integration of the vector can be identified because the Green fluorescent protein is found when a cancer cell has been infected with the retrovirus expression vector. For this purpose, MFG-IRES-Puro or a MFG-IRES-GFP vector including the expression cassette containing LTR promoter site, multiple cloning site, the IRES, puro or GFP gene, late polyadnylation signal site was used. RT-PCR was performed using RNA isolated from normal tissues as a template to obtain a normal human p31$^{comet}$ gene. The recombinant retrovirus vector Retro-IRES/p31$^{comet}$ capable of expressing the p31$^{comet}$ protein was obtained by inserting the obtained cDNA of p31$^{comet}$ into the multiple cloning sites of MFG-IRES-Puro or MFG-IRES-GFP vectors.

Some promoters useful for practice of the present invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus (CMV) immediate-early, retroviral LTR, metallothionein, SV-40, adenovirus E1a, and adenovirus major late (MLP) promoters.

According to another aspect of the present invention, there is provided a microorganism transformed with the recombinant virus vector pAdeno-CMV/p31$^{comet}$-IRES/GFP or Retro-IRES/p31$^{comet}$ being bacterial cells, yeast cells or mammalian cells, etc.

According to another aspect of the present invention, there is provided a method of preparing a recombinant p31$^{comet}$ protein including cultivating mammalian cells transfected with the recombinant virus vector pAdeno-CMV/p31$^{comet}$-IRES/GFP or Retro-IRES/p31$^{comet}$.

A pharmaceutical composition for the treatment of malignant tumors of an embodiment of the present invention may include the recombinant virus vector pAdeno-CMV/p31$^{comet}$-IRES/GFP or Retro-IRES/p31$^{comet}$, p31$^{comet}$ RNA transcribed from the p31$^{comet}$ gene or a protein represented by SEQ ID NO: 3 or 4 as an effective component. The p31$^{comet}$ protein mass-produced by cells transfected with the recombinant virus vectors or RNA transcripted from the p31$^{comet}$ gene can be used as an effective component of the pharmaceutical composition. Preferably, expression vectors can be used as an effective component due to the continuous production of the recombinant protein by the expression vectors. Accordingly, the expression vectors of an embodiment of the present invention can be used as an effective component of the pharmaceutical composition for gene therapy.

According to another aspect of the present invention, there is provided a recombinant adenovirus pAdeno-CMV/p31$^{comet}$-IRES/GFP not including a transduced proliferous variant virus. Adenoviruses are DNA viruses including an essential E1A gene for proliferating the virus and essential genes for packaging the virus. The proliferating gene of the adenovirus should be removed to prevent the virus from proliferating in the human body for the purpose of the gene therapy. When the E1A gene region related to the proliferation of the adenovirus is removed, the adenovirus cannot proliferate in a normal cell and can be used for the gene therapy. To obtain the adenovirus in a large quantity using the adenovirus expression vector, the cell line capable of packaging the adenovirus is transfected with the expression vector. A 293 cell is used as a packaging cell line. Because a 293 cell includes the E1 gene region of adenovirus in its chromosomal DNA, the E1A gene is continuously expressed and E1A proteins are provided to the cell. The adenovirus expression vector pAdeno-CMV/p31$^{comet}$-IRES/GFP according to an embodiment of the present invention is injected together with the adenovirus parent vector into the packaging cell 293. An adenovirus clone not including the proliferous recombinant variant virus is selected and provided.

According to another aspect of the present invention, there is provided a recombinant retrovirus Retro-IRES/p31$^{comet}$ not including the transduced proliferous variant virus. An LN type plasmid designed by Dr. Dusty Miller has been used as a retrovirus vector in gene therapy for cancers and genetic metabolic diseases. The LN type plasmid can be transfected or transducted into a packaging cell line of PA317. In addition, an MFG type plasmid designed by R. Mulligan, et al. has been recently used for clinical purposes. Like the LN type plasmid, the MFG type plasmid is based on the moloney leukemia virus (MLV). The MFG type plasmid is useful for the expression of enzymes since the gene inserted site which is the restriction enzyme site of NcoI is modified to be a start codon. The expression vector is transducted into the H29D packaging cell line to prepare virus particles and non-proliferous expression viruses are selected.

According to another aspect of the present invention, there is provided a microarray for the diagnosis of a malignant tumor adhered to a support including the entire or part of probe of the p31$^{comet}$ gene represented by SEQ ID NO: 1 or 2, or the antibody to the p31$^{comet}$ protein represented by SEQ ID NO: 3 or 4. The support of the microarray may be a glass slide, a membrane, a semiconductor chip, silicon or gel, but is not limited thereto.

The probe of the microarray may be any biological material capable of detecting a malignant tumor according to the type of the microarray. The probe may be a DNA analog such as cDNA, an oligonucleotide, peptide nucleic acid (PNA), locked nucleic acid (LNA), hexitol nucleic acid (HNA), a peptide or a protein. The malignant tumor may be a solid tumor of uterine cervix cancer, ovarian cancer, liver cancer, breast cancer, lung cancer, bone cancer, kidney cancer, pancreatic cancer, gastric cancer or colorectal cancer.

According to another aspect of the present invention, there is provided a diagnostic kit for malignant tumors including the microarray. The diagnostic kit may further include a hybridization reaction solution, a PCR kit including primers for the amplification of the target product, a non-hybridized reaction DNA washing solution, a cover slip, a stain, a non-stain binding washing solution and guidelines in addition to the microarray.

Advantageous Effects

The pharmaceutical composition of the present invention can suppress cancer cell growth, induce apoptosis and kill cells by overexpressing p31$^{comet}$ in solid malignant tumor cells. Therefore, the pharmaceutical composition can be effectively used for gene therapy.

BEST MODE

Hereinafter, the present invention will be described more specifically with reference to the following examples. However, the following examples are provided only for illustrations and thus the present invention is not limited to or by them.

General Molecular Biology Techniques

Methods traditionally used in molecular biology, such as preparative extraction of plasmid DNA, centrifugation of plasmid DNA in a cesium chloride gradient, agarose or acrylamide gel electrophoresis, purification of DNA fragments by electroelution, protein extraction with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; ($2^{nd}$ Ed. 1989); Ausubel F. M. et al. (eds), "Current Protocols in Molecular Biology", John Wiley & Sons, New York, 1987].

Conventional cloning vehicles include pBR322 and pUC type plasmids and phages of the M13 series. These may be obtained commercially (Bethesda Research Laboratories).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed through a controlled treatment with S1 nuclease.

The enzymatic amplification of DNA fragments using a PCR [Polymerase-catalyzed Chain Reaction, Saiki R. K. et al., Science 230 (1985) 1350-1354; Mullis K. B. and Faloona F. A., Meth. Enzym. 155 (1987) 335-350] technique may be performed using a "DNA thermal cycler" (Perkin Elmer Cetus) according to the manufacturer's specifications.

Verification of nucleotide sequences may be performed through the method developed by Sanger et al. [Proc. Natl. Acad. Sci. USA, 74 (1977) 5463-5467] using the kit distributed by Amersham.

Plasmid DNAs may be purified by the Qiagen Plasmid Purification System according to the manufacture's instruction.

Example 1

Preparing Adenovirus Vector Expressing $p31^{comet}$-1 and 2

Figure 1:
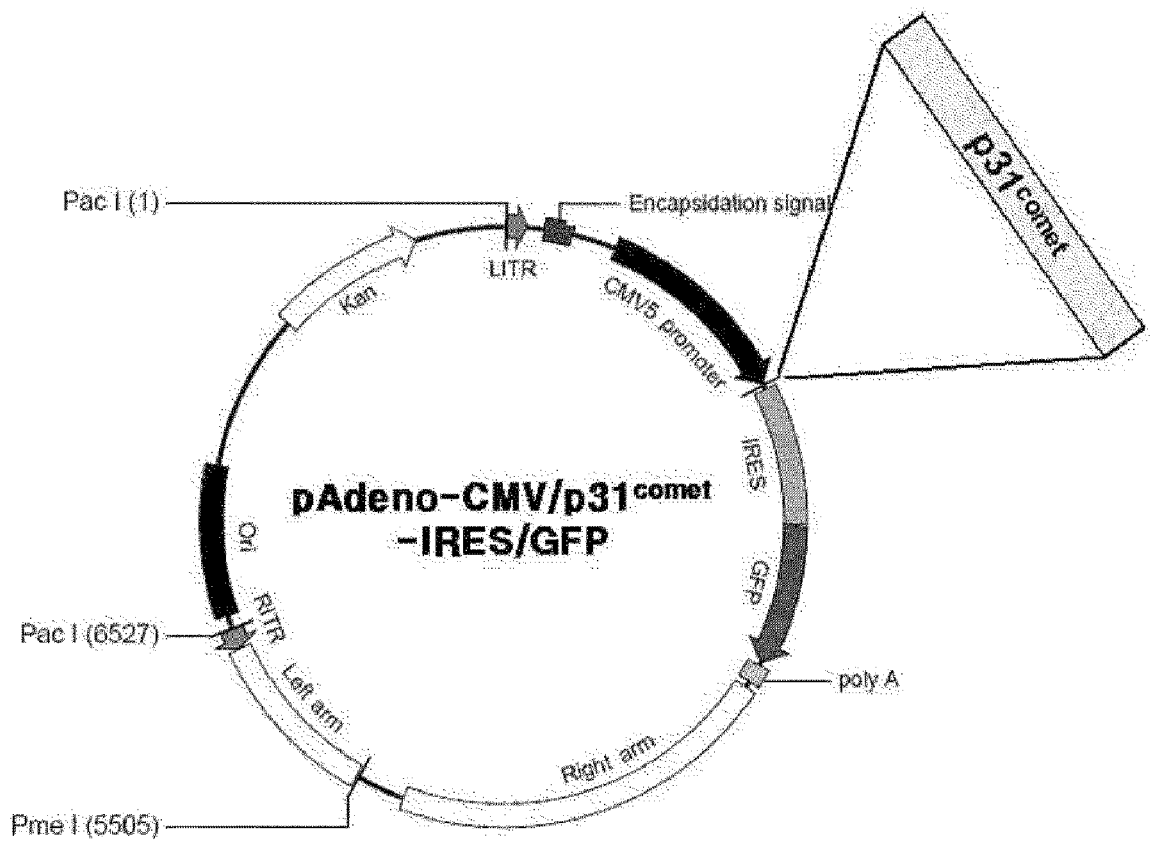
FIG. 1 is a cleavage map illustrating a recombinant adenovirus vector pAdeno-CMV/p31$^{comet}$-IRES/GFP.

Normal human $p31^{comet}$ cDNA was obtained from the human thymus library of Clontech through a PCR using a forward primer (SEQ ID NO: 5) and a reverse primer (SEQ ID NO: 6) to isolate the $p31^{comet}$ gene. The PCR was performed using a 50 μl mixture containing 0.1 μg of the library, each 10 pmol of the forward and reverse primers, 10 units of Tag polymerase (Takara), a 1× buffer solution, 2.5 mM dNTPs and water. The template DNA was denatured at 95° C. for 5 minutes, cycled 30 times (95° C. for 45 seconds, 56° C. for 45 seconds, and 72° C. for 1 minute) for the amplification of $p31^{comet}$ cDNA, and then further amplification was performed at 72° C. for 10 minutes. The amplified $p31^{comet}$ cDNA was separated using a column. The cDNA of $p31^{comet}$ and the vector were cleaved with Bal II restriction enzyme and the cDNA was separated to insert into the multiple cloning site of a pAdenoVator-CMV5-IRES-GFP vector. The separated cDNA corresponds to the $37^{th}$ through $861^{st}$ sites of SEQ ID NO: 2. After the separated $p31^{comet}$ was ligated to the vector, DH-5α, which is a transformation host, was transformed. Among the vectors, appropriately prepared pAdeno-CMV/$p31^{comet}$-IRES/GFP was selected and mass-produced. $p31^{comet}$-1 and $p31^{comet}$-2 genes were produced in the same manner. FIG. 1 is a cleavage map illustrating the pAdeno-CMV/$p31^{comet}$-IRES/GFP vector.

Figure 2:
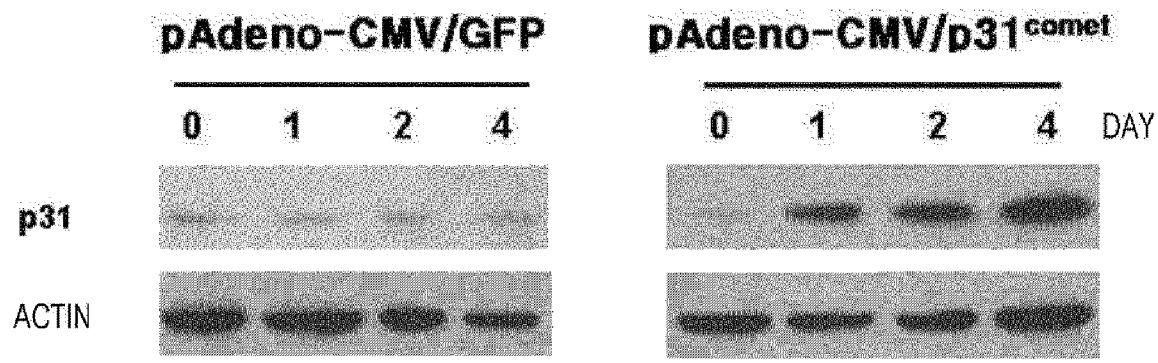
FIG. 2 illustrates the expressed amount of a pAdeno-CMV/p31$^{comet}$-IRES/GFP vector measured by Western blotting according to time.

Additionally, 293 cell was used to produce the virus and an adenovirus clone not including a proliferous variant virus was identified. To identify normal expression of the prepared pAdeno-CMV/$p31^{comet}$-IRES/GFP vector, the adenovirus was infected into a HeLa cell and the expression over time was identified. FIG. 2 illustrates the expressed amount of the pAdeno-CMV/$p31^{comet}$-IRES/GFP vector measured by Western blotting. A known conventional Western blotting method was used. In FIG. 2, the left panel illustrates a negative control in which the $p31^{comet}$ gene is not inserted, and actin is a positive control showing that the amount of protein separated from the negative control is almost the same as the amount of the protein of the present invention. As illustrated in FIG. 2, the adenovirus vector of the present invention expresses the $p31^{comet}$ protein far more than the negative control over time.

Example 2

Preparing Retrovirus Vector Expressing $p31^{comet}$-1 and 2

Figure 3:
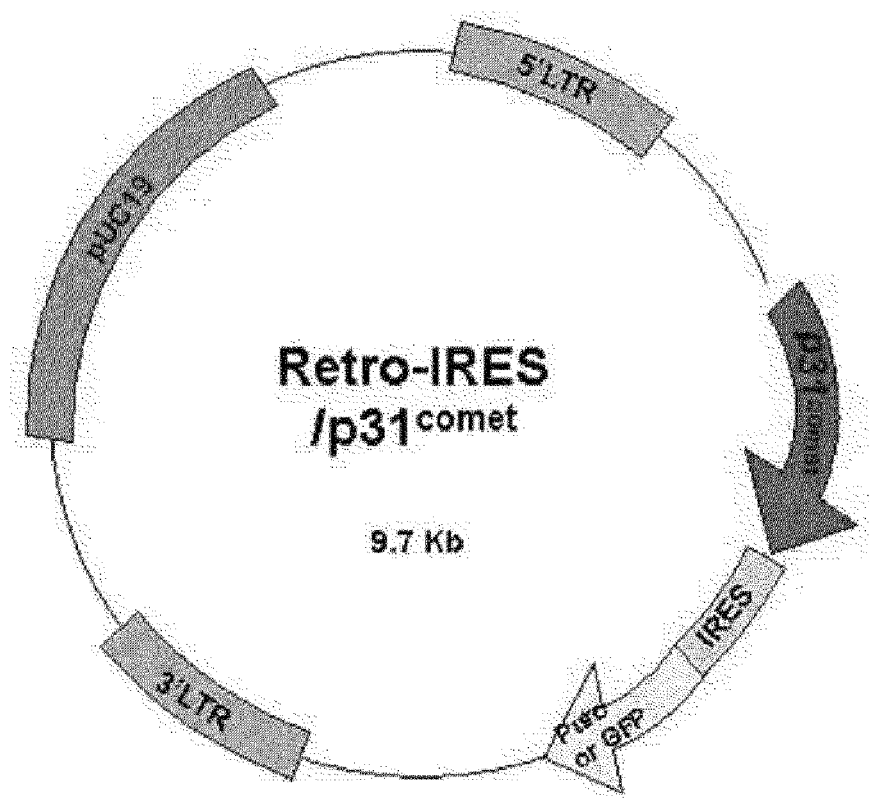
FIG. 3 is a cleavage map illustrating a recombinant retrovirus vector Retro-IRES/p31$^{comet}$.
Figure 4:
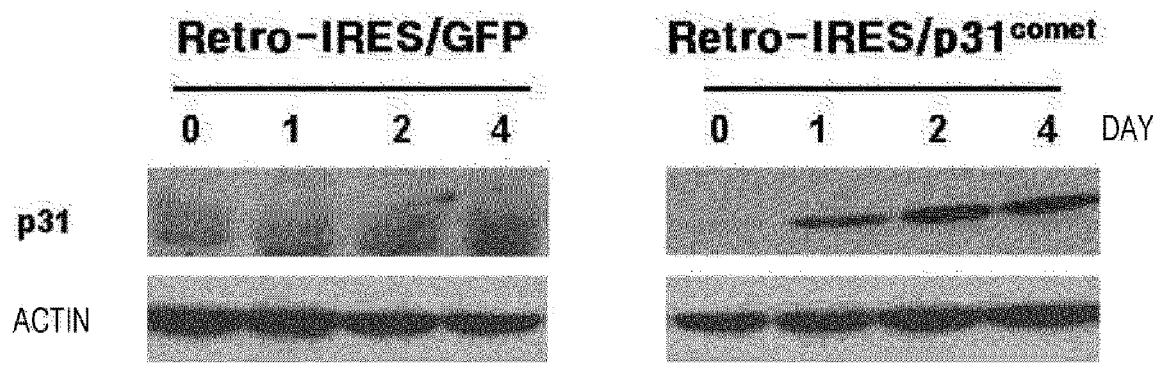
FIG. 4 illustrates the expressed amount of a Retro-IRES/p31$^{comet}$ vector measured by Western blotting according to time.

Retrovirus vectors including the $p31^{comet}$ gene were prepared in a similar manner to the adenovirus vectors in Example 1. FIG. 3 is a cleavage map illustrating the Retro-IRES/$p31^{comet}$ vector. The inventors of the present invention produced the virus including the gene that is non-proliferous variant virus using an H29D packtaging cell. To identify the expression of the $p31^{comet}$ protein, the retrovirus was infected into a HeLa cell and the expression over time was identified. FIG. 4 illustrates the expressed amount of the Retro-IRES/$p31^{comet}$ vector measured by Western blotting over time. In FIG. 4, the left panel illustrates a negative control in which the $p31^{comet}$ gene is not inserted, and actin is a positive control showing that the amount of protein separated from the negative control is almost the same as the amount of the protein of the present invention. As illustrated in FIG. 4, it is identified that the retrovirus vector of the present invention expresses the $p31^{comet}$ protein far more than the negative control.

Example 3

Effect of $p31^{comet}$ on the Growth Suppression of Cancer Cells

In order to identify the effect of $p31^{comet}$ on cancer cells, 20 types of cancer cell lines were used in total. In detail, 5 of uterine cervix cancer cell lines (HeLa, SW756, SiHa, MS751 and Caski); 5 kinds of lung cancer cell lines (A549, Calu-1, Sk-Lu-1, H460 and H446); 5 of liver cancer cell lines (Sk-Hep-1, Chang, HepG2, Huh-7 and Hep3B); 2 of bone cancer cell lines (SaOs-2 and U-2OS); 2 of breast cancer cell lines (MCF-7 and T47D); and 1 of kidney cancer cell line (293) were used.

Figure 5:
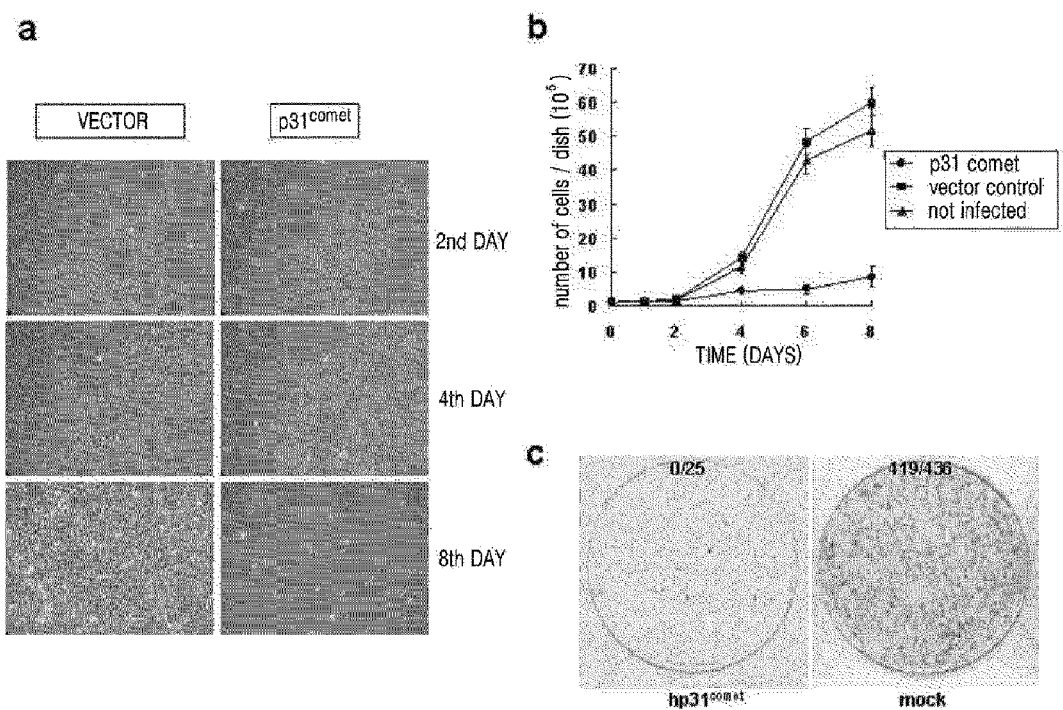
FIG. 5A a is a comparison of cell shape between p31$^{comet}$ and a control group.
FIG. 5B is a proliferation analysis of cells infected by p31$^{comet}$ and the control group.
FIG. 5C is a colony forming analysis of cells infected by p31$^{comet}$ and the control group.

Among the 20 of human cancer cell lines, HeLa, SW756, SiHa, MS751, Sk-Lu-1, Sk-Hep-1, HepG2, Hep3B, MCF-7, T47D and 293 were cultivated in wet conditions including 10% FBS (JRH Biosciences Inc. Kansas, USA), and MEM (WelGENE Inc. Daegu, South Korea) including streptomycin and penicillin G at 37° C. with 5% $CO_2$. The Caski, A549, H460, H446 and Huh-7 cell lines were cultivated in wet conditions including 10% FBS (JRH Biosciences Inc. Kansas, USA), RPMI (WelGENE Inc. Daegu, South Korea) including streptomycin and penicillin G at 37° C. with 5% $CO_2$. The Calu-1, SaOs-2 and U-2OS cell lines were cultivated in wet conditions including 10% FBS (JRH Biosciences Inc. Kansas, USA), and McCoy (WelGENE Inc. Daegu, South Korea) including streptomycin and penicillin G at 37° C. with 5% $CO_2$. The Chang cell line was cultivated in moist conditions including 10% FBS (JRH Biosciences Inc. Kansas, USA), and DMEM (WelGENE Inc. Daegu, South Korea) including streptomycin and penicillin G at 37° C. with 5% $CO_2$. In order to identify the effect of $p31^{comet}$ on the growth of cancer cells, the cancer cells were cultivated in a concentration of $2×10^5$ cells/well in 6 well plates (Nalge Nunc, Naperville, Ill.) for a day. The retrovirus including Retro-IRES/$p31^{comet}$, the multiplicity of infection (moi) of which was optimized for each cell, was added to each medium-removed well and shaken at intervals of 15 minutes for 2 hours. After 2 hours, 2 ml of a medium was added to each of the wells including the viruses and the cells were cultivated. The medium was changed after 12 to 24 hours and then 700 to 1000 cells were spreaded into a 100 mm plate. When a colony having an appropriate size for counting was formed after 9 to 12 days, the colonies showing green fluorescence and colonies not showing green fluorescence were counted using a fluorescence microscope. In the case of A549, for example, as shown in panel c of FIG. 5, p31 overexpressed cells showed remarkably decreased colony formation in comparison with the control. Also, other cells showed the same results as A549 (referred to as FIG. 6). 100% inhibition of colony formation was observed in all cancer cell lines except the liver cancer cell line HepG2 in which colony formation was reduced by 75% and the uterine cancer cell line H460 in which colony formation was reduced by 84%. That is, it was determined that p31$^{comet}$ overexpressed cells cannot form colonies and thus cells cannot grow at all. It was also identified that p31$^{comet}$ completely inhibits the growth of cancer cells.

Example 4

Analysis of Suppression of Cancer Cell Proliferation by p31$^{comet}$

In order to analyze the suppression of cancer cell proliferation by p31$^{comet}$ in Example 3, a retrovirus including Retro-IRES/p31$^{comet}$ was infected into A549, Calu-1 etc.

<4-1> Measuring p31$^{comet}$ Overexpressed Cell Growth

The number of cells infected with the retrovirus including Retro-IRES/p31$^{comet}$ was measured daily. The cells of the control proliferated normally but the p31 comet overexpressed cells hardly proliferated (refer to panel b of FIG. 5B). The size of the cells was observed with a microscope after 8 days. It was found that the p31$^{comet}$ infected cells were 10 to 30 times larger than the cells of the control (refer to pane a of FIG. 5).

<4-2> Senescence Associated-β-Galactosidase (SA-β-Gal) Test

Figure 7:
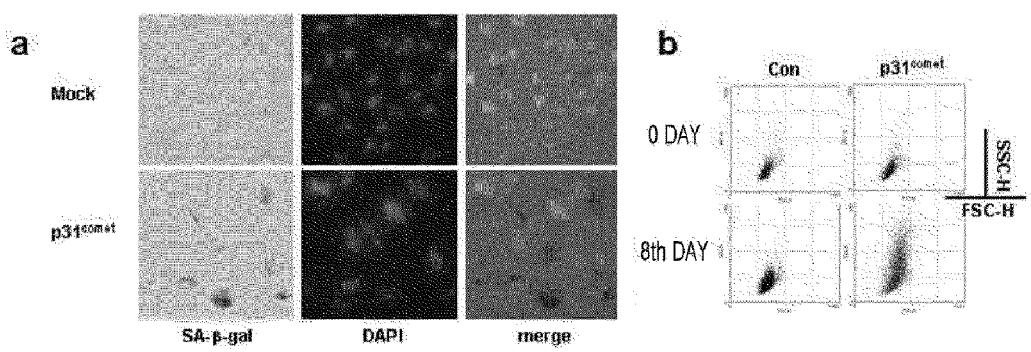
FIG. 7A illustrates the results of a SA-β-gal test on A549 cells infected with p31$^{comet}$ and the control group.
FIG. 7B illustrates analysis results obtained from the results illustrated in FIG. 7A using a fluorescent activated cell sorter.

A Senescence Associated-β-galactosidase (SA-β-gal) test was performed to inspect the relationship between the enlarged cell size observed in Example 4-1 and the senescence of cells. The infected cells and the control cells in 60 mm dishes were collected daily, were washed three times with phosphate buffered saline (PBS), treated with a PBS fixing fluid including 2% formaldehyde and 0.2% glutaraldehyde for 10 minutes and washed again three times with PBS. The washed cells were reacted in a stain solution of PBS including 5 mM potassium ferricyanide, 5 mM ferrocyanide, and 1 mg/ml of X-gal (4% (v/v) in dimethylformamide in an incubator at 37° C. for 12 hours and washed with PBS. The cells were observed with an optical microscope and a fluorescence microscope after reacting with a stain solution of PBS including 50 ng of DAPI capable of staining the cell nucleus at room temperature for about 1 hour. As a result, 80% of the p31$^{comet}$ infected cells were stained with SA-β-gal and 2 to 6% of the cells of the control were stained. In addition, the size of the nuclei of the p31 comet infected cells were enlarged, showing an abnormal nucleus shape (refer to panel a of FIG. 7). These features can be considered as senescence indicating that p31$^{comet}$ infected cancer cells rapidly enter senescence and can not grow any further.

<4-3> Measuring Cell Aging Using Fluorescent Activated Cell Sorter (FACS)

In order to show the aging of cells of Example 4-2 more clearly, the level of cell aging was measured using a FACS. In a FACS, the size of cells and the amount of particulars in the cells can be measured using a laser beam. The SSC value indicating the number of particulars in uterine cervix cells infected with p31$^{comet}$ was found to be remarkably large in comparison with the control (refer to panel b of FIG. 7).

<4-4> Measuring Proliferation and Death of Cells Using MTT Assay

Figure 8:
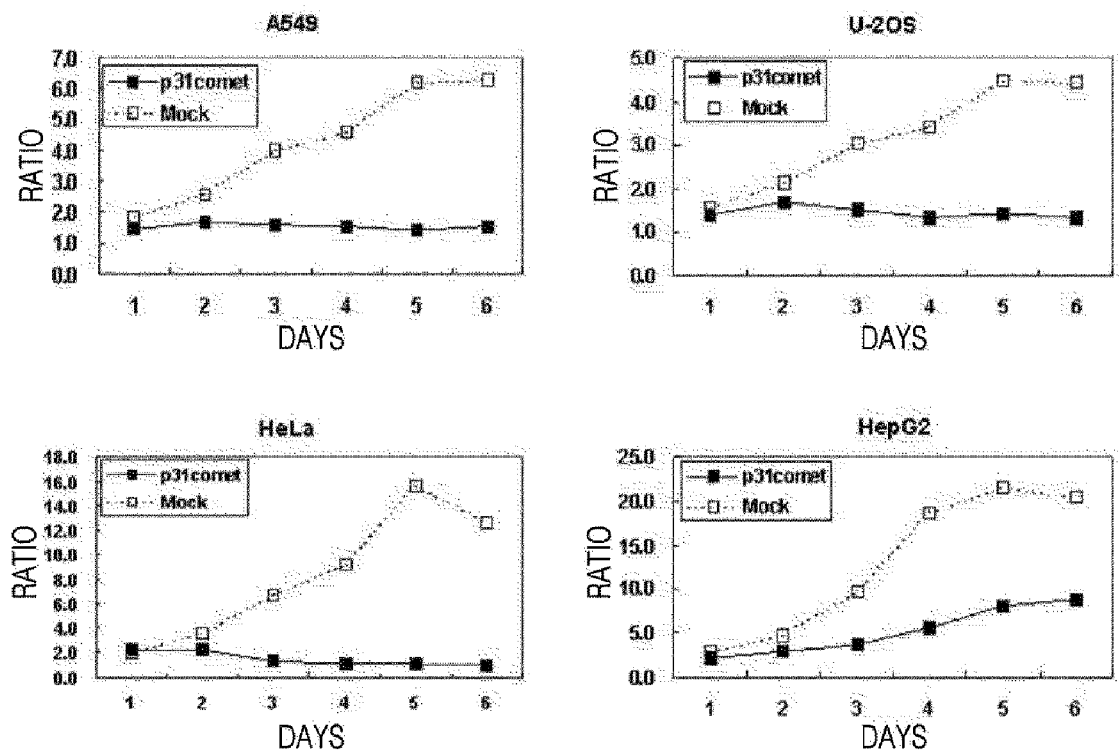
FIG. 8 illustrates the death of A549, U-2OS, HeLa and HepG2 cells infected with p31$^{comet}$ and the control group using MTT assay.

An MTT assay was performed to identify features besides aging in uterine cervix cells measured in Examples 4-2 and 4-3. When 3-[4,5-dimethylthiazol-2-yl]-2,5-di-phenyltetrazolium bromide (MTT) reacts with a specific enzyme in the mitochondria of a live cell, a blue crystal forms. The survival ratio was identified by the intensity of blue. A549, HeLa, U-205 and HepG2 cells in a concentration of 1–3×10$^5$/well were respectively infected with 40, 16, 25, and 50 moi of an adenovirus including pAdeno-CMV/p31$^{comet}$-IRES/GFP in 6 well plates. The intensity of blue in the infected cells was measured on various dates with ELISA and the results were compared with results obtained from the cells of the control (refer to FIG. 8). While the numbers of HeLa and U-205 cells rapidly decreased after 2 days after the infection, the number of cells of the control increased normally. The number of A549 live cells gradually decreased. The decrease in cell numbers is considered to have been caused by growth suppression due to the aging of A549 (refer FIGS. 5 and 7). The increase in number of live HepG2 cells was far lower than that of the control, proving growth suppression due to the overexpressed p31$^{comet}$.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for the inhibiting growth of tumor cells, comprising
introducing a human p31$^{comet}$ gene encoding a protein of sequence SEQ ID NO: 3 or 4 to solid tumor cells in vitro, wherein the human p31$^{comet}$ gene is present in a viral vector that overexpresses the encoded protein.

2. The method of claim 1, wherein the human p31$^{comet}$ gene is of sequence SEQ ID NO: 1 or 2.

3. The method of claim 1, wherein the viral vector is selected from the group consisting of a retrovirus, an adenovirus, an adeno-associated virus (AAV), a herpes simplex virus and a lentivirus.

4. The method of claim 3, wherein a promoter used in the vector is selected from the group consisting of insulin promoter, whey acidic protein promoter, tyrosinase promoter, glial fibrillary acidic protein promoter, albumin promoter, CEA promoter, T-cell receptor promoter, a-Fetoprotein (AFP) promoter, circulatory luekoprotease inhibitor (CLPI) promoter, Her 2/neu promoter, Myc-Max responsive element promoter, MUC-1 promoter, osteocalcin promoter, MCK promoter, MBP promoter, GFAP promoter, NSE promoter, prostate-specific antigen (PSA) promoter, prostate-specific membrane antigen (PSMA) promoter, probasin promoter, human glandular kallikrein (hK2) promoter, myelin basic protein (MBP) promoter, myelin proteolipid protein promoter, neural specific enolase promoter, neuronal specific synapsin 1 promoter, Ncx/Hox11L.1 promoter, surfactant protein B promoter, thyroglobulin promoter, ovarian-specific promoter, telomerase promoter, Erb B2 promoter, DF3/MUC1 promoter, L-plastin promoter, SLP1 promoter, alpha lactalbumin promoter, somatostatin promoter, Cox2 promoter, ornithine decarboxylase promoter, gastrin-releasing peptide promoter, metallothionein promoter, calponin promoter, H19 promoter, Tcf promoter, calretinin promoter, Cdc25C promoter, cyclin A promoter, endoglin promoter, IGF-1-R promoter, E2F-1 promoter, KDR/Flk-1 promoter, Flt-1 promoter, E-selectin promoter, vWF promoter, preproendothelin-1 promoter, VCAM-1 promoter, VEGF promoter, erythropoietin promoter, phosphoglycerate kinase 1 promoter, GRP78 promoter, hexokinase II promoter, Erg-1 and CArG elements promoter, Waf-1 promoter, RecA promoter, c-IAP2 promoter, HSP70B promoter, Gadd 153 promoter, MDR-1 promoter, tetracycline inducible promoter, rapamycin inducible promoter and tamoxifen-inducible estrogen response elements promoter.

5. The method of claim 3, wherein the vector is a recombinant adenovirus vector pAdeno-CMV/p31$^{comet}$-IRES/GFP or a recombinant retrovirus vector Retro-IRES/p31$^{comet}$.

6. A method for inhibiting growth of malignant tumors, comprising
introducing a recombinant virus vector pAdeno-CMV/p31$^{comet}$-IRES/GFP or Retro-IRES/p31$^{comet}$ to solid tumor cells in vitro.

7. The method according to claim 1, wherein the tumor is selected from the group consisting of uterine cervix cancer, ovarian cancer, liver cancer, breast cancer, lung cancer, bone cancer, kidney cancer, pancreatic cancer, gastric cancer, and colorectal cancer.

8. The method according to claim 6, wherein the malignant tumor is selected from the group consisting of uterine cervix cancer, ovarian cancer, liver cancer, breast cancer, lung cancer, bone cancer, kidney cancer, pancreatic cancer, gastric cancer, and colorectal cancer.

* * * * *

SEQUENCE LISTING

<160> NUMBER OF SEQ ID NOS: 6

<210> SEQ ID NO 1
<211> LENGTH: 1550
<212> TYPE: DNA
<213> ORGANISM: Homo sapiens

<400> SEQUENCE: 1
gggaatttag agcctcgagg cctggggtgg ggacgcgagg acaccagcgt agaagagctt    60
acatcagaat cgagctttgt gggcgctccg ggatttggcc ctttagcgcg gatcctagac   120
aacaggtttt ggacctcgag agctgcagaa ctgaggctac tggtgccgcc agcctgctgg   180

```
ctccgcctct gcctcagttt cttccctat ggcccgcgtg ccgctggggc ggagtctcac    240
tctgtcaccc aggctggagc acaatggcat gacctcagct caccacaact tccgcctccc    300
aggttcaagg gattctcctg cctcagcctc ccaagtagct gagattatag atttggagtg    360
gtatgagaag tccgaagaaa ctcacgcctc ccagatagaa ctacttgaga caagctctac    420
gcaggaacct ctcaacgctt cggaggcctt tgcccaaga gactgcatgg taccagtggt    480
gtttcctggg cctgtgagcc aggaaggctg ctgtcagttt acttgtgaac ttctaaagca    540
tatcatgtat caacgccagc agctccctct gccctatgaa cagcttaagc acttttaccg    600
aaaaccttct ccccaggcag aggagatgct gaagaagaaa cctcgggcca ccactgaggt    660
gagcagcagg aaatgccaac aagccctggc agaactggag agtgtcctca gccacctgga    720
ggacttcttt gcacggacac tagtaccgcg agtgctgatt ctccttgggg caatgccct    780 aagccccaag gagttctatg aactcgactt gtctctgctg gcccctaca gcgtggacca    840 gagcctgagc acagcagctt gtttgcgccg tctcttccga gccatattca tggctgatgc    900 cttagcgag cttcaggctc ctccactcat gggcaccgtc gtcatggcac agggacaccg    960
caactgtgga aagattggt ttcgacccaa gctcaactat cgagtgccca gccggggcca   1020
taaactgact gtgaccctgt catgtggcag accttccatc cgaaccacgg cttgggaaga   1080
ctacatttgg ttccaggcac cagtgacatt taaaggcttc cgcgagtgaa tgagtgcttc   1140
ttaatcctaa aaacacaatg gctgaattat ctttctccat gtggcgctga atcacccatc   1200
tggtttggag ctagagttgc ttcctggtga gagaggaagc aactctcctt ctggttgtct   1260
gcctcccctc agatttcctg ataggctgat ggcatgtggc tgtgactgtg actgtaatca   1320
ttgctgaaca acatctcttt gaatcaaagg ttgattttcc cagagggtgc tgggtcaggc   1380
atttctatta ggagttggaa agcaaaaatg ggtccataga cactctatgg aggtgtccct   1440
ttctgctctt tgctgtgtcc tttcagaatt tttaccagga acataatgtg gatgtgactt   1500
atgaacttaa atataaaata aatagattct tattatattt tcctgaaaaa              1550
```

<210> SEQ ID NO 2
<211> LENGTH: 1283
<212> TYPE: DNA
<213> ORGANISM: Homo sapiens

<400> SEQUENCE: 2

```
attctaaccg caaggagtag cggaggggag gtcgtgatgg cggcgccgga ggcggaggtt     60
ctgtcctcag ccgcagtccc tgatttggag tggtatgaga agtccgaaga aactcacgcc    120
tcccagatag aactacttga gacaagctct acgcaggaac ctctcaacgc ttcggaggcc    180
ttttgcccaa gagactgcat ggtaccagtg gtgtttcctg ggcctgtgag ccaggaaggc    240
tgctgtcagt ttacttgtga acttctaaag catatcatgt atcaacgcca gcagctccct    300
ctgccctatg aacagcttaa gcacttttac cgaaaaacctt ctccccaggc agaggagatg    360
ctgaagaaga aacctcgggc caccactgag gtgagcagca ggaaatgcca acaagccctg    420
gcagaactgg agagtgtcct cagccacctg gaggacttct ttgcacggac actagtaccg    480
cgagtgctga ttctccttgg gggcaatgcc ctaagcccca aggagttcta tgaactcgac    540
ttgtctctgc tggccccta cagcgtggac cagagcctga gcacagcagc ttgtttgcgc    600
cgtctcttcc gagccatatt catggctgat gcctttagcg agcttcaggc tcctccactc    660
atgggcaccg tcgtcatggc acagggacac cgcaactgtg gagaagattg gtttcgaccc    720
aagctcaact atcgagtgcc cagccggggc cataaactga ctgtgaccct gtcatgtggc    780
```

-continued

```
agaccttcca tccgaaccac ggcttgggaa gactacattt ggttccaggc accagtgaca    840
tttaaaggct tccgcgagtg aatgagtgct tcttaatcct aaaaacacaa tggctgaatt    900
atctttctcc atgtggcgct gaatcaccca tctggtttgg agctagagtt gcttcctggt    960
gagagaggaa gcaactctcc ttctggttgt ctgcctcccc tcagatttcc tgataggctg   1020
atggcatgtg gctgtgactg tgactgtaat cattgctgaa caacatctct ttgaatcaaa   1080
ggttgatttt cccagagggt gctgggtcag gcatttctat taggagttgg aaagcaaaaa   1140
tgggtccata gacactctat ggaggtgtcc ctttctgctc tttgctgtgt cctttcagaa   1200
tttttaccag gaacataatg tggatgtgac ttatgaactt aaatataaaa taaatagatt   1260
cttattatat tttcctgaaa aaa                                          1283
```

<210> SEQ ID NO 3
<211> LENGTH: 306
<212> TYPE: PRT
<213> ORGANISM: Homo sapiens

<400> SEQUENCE: 3

```
Met Ala Arg Val Pro Leu Gly Arg Ser Leu Thr Leu Ser Pro Arg Leu
  1               5                  10                  15

Glu His Asn Gly Met Thr Ser Ala His His Asn Phe Arg Leu Pro Gly
                 20                  25                  30

Ser Arg Asp Ser Pro Ala Ser Ala Ser Gln Val Ala Glu Ile Ile Asp
             35                  40                  45

Leu Glu Trp Tyr Glu Lys Ser Glu Glu Thr His Ala Ser Gln Ile Glu
     50                  55                  60

Leu Leu Glu Thr Ser Ser Thr Gln Glu Pro Leu Asn Ala Ser Glu Ala
 65                  70                  75                  80

Phe Cys Pro Arg Asp Cys Met Val Pro Val Phe Pro Gly Pro Val
                 85                  90                  95

Ser Gln Glu Gly Cys Cys Gln Phe Thr Cys Glu Leu Leu Lys His Ile
            100                 105                 110

Met Tyr Gln Arg Gln Leu Pro Leu Pro Tyr Glu Gln Leu Lys His
        115                 120                 125

Phe Tyr Arg Lys Pro Ser Pro Gln Ala Glu Glu Met Leu Lys Lys Lys
    130                 135                 140

Pro Arg Ala Thr Thr Glu Val Ser Ser Arg Lys Cys Gln Gln Ala Leu
145                 150                 155                 160

Ala Glu Leu Glu Ser Val Leu Ser His Leu Glu Asp Phe Phe Ala Arg
                165                 170                 175

Thr Leu Val Pro Arg Val Leu Ile Leu Leu Gly Gly Asn Ala Leu Ser
            180                 185                 190

Pro Lys Glu Phe Tyr Glu Leu Asp Leu Ser Leu Leu Ala Pro Tyr Ser
        195                 200                 205

Val Asp Gln Ser Leu Ser Thr Ala Ala Cys Leu Arg Arg Leu Phe Arg
    210                 215                 220

Ala Ile Phe Met Ala Asp Ala Phe Ser Glu Leu Gln Ala Pro Pro Leu
225                 230                 235                 240

Met Gly Thr Val Val Met Ala Gln Gly His Arg Asn Cys Gly Glu Asp
                245                 250                 255

Trp Phe Arg Pro Lys Leu Asn Tyr Arg Val Pro Ser Arg Gly His Lys
            260                 265                 270

Leu Thr Val Thr Leu Ser Cys Gly Arg Pro Ser Ile Arg Thr Thr Ala
        275                 280                 285
```

```
Trp Glu Asp Tyr Ile Trp Phe Gln Ala Pro Val Thr Phe Lys Gly Phe
        290                 295                 300

Arg Glu
305

<210> SEQ ID NO 4
<211> LENGTH: 274
<212> TYPE: PRT
<213> ORGANISM: Homo sapiens

<400> SEQUENCE: 4

Met Ala Ala Pro Glu Ala Glu Val Leu Ser Ser Ala Ala Val Pro Asp
  1               5                  10                  15

Leu Glu Trp Tyr Glu Lys Ser Glu Glu Thr His Ala Ser Gln Ile Glu
                 20                  25                  30

Leu Leu Glu Thr Ser Ser Thr Gln Glu Pro Leu Asn Ala Ser Glu Ala
             35                  40                  45

Phe Cys Pro Arg Asp Cys Met Val Pro Val Val Phe Pro Gly Pro Val
 50                  55                  60

Ser Gln Glu Gly Cys Cys Gln Phe Thr Cys Glu Leu Leu Lys His Ile
 65                  70                  75                  80

Met Tyr Gln Arg Gln Gln Leu Pro Leu Pro Tyr Glu Gln Leu Lys His
                 85                  90                  95

Phe Tyr Arg Lys Pro Ser Pro Gln Ala Glu Glu Met Leu Lys Lys Lys
            100                 105                 110

Pro Arg Ala Thr Thr Glu Val Ser Ser Arg Lys Cys Gln Gln Ala Leu
            115                 120                 125

Ala Glu Leu Glu Ser Val Leu Ser His Leu Glu Asp Phe Phe Ala Arg
130                 135                 140

Thr Leu Val Pro Arg Val Leu Ile Leu Leu Gly Gly Asn Ala Leu Ser
145                 150                 155                 160

Pro Lys Glu Phe Tyr Glu Leu Asp Leu Ser Leu Leu Ala Pro Tyr Ser
                165                 170                 175

Val Asp Gln Ser Leu Ser Thr Ala Ala Cys Leu Arg Arg Leu Phe Arg
            180                 185                 190

Ala Ile Phe Met Ala Asp Ala Phe Ser Glu Leu Gln Ala Pro Pro Leu
            195                 200                 205

Met Gly Thr Val Val Met Ala Gln Gly His Arg Asn Cys Gly Glu Asp
210                 215                 220

Trp Phe Arg Pro Lys Leu Asn Tyr Arg Val Pro Ser Arg Gly His Lys
225                 230                 235                 240

Leu Thr Val Thr Leu Ser Cys Gly Arg Pro Ser Ile Arg Thr Thr Ala
                245                 250                 255

Trp Glu Asp Tyr Ile Trp Phe Gln Ala Pro Val Thr Phe Lys Gly Phe
                260                 265                 270

Arg Glu

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
agaagatcta tggattacaa ggatgac                                     27
```

```
<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tgcagatctt caggtcacag tcagtttatg                                    30
```